United States Patent [19]

Olivieri et al.

[11] 4,332,905

[45] Jun. 1, 1982

[54] PROCESS FOR PREPARING CARBAMYL DERIVATIVES OF α-HYDROXY ACIDS AND THE CORRESPONDING α-HYDROXY ACIDS

[75] Inventors: Roberto Olivieri, Mentana; Giancarlo Eletti Bianchi, Rome; Eugenio Fascetti, Rome; Felice Centini, Rome; Ludwig Degen, Rome; Walter Marconi, San Donato Milanese, all of Italy

[73] Assignee: E.N.I. Ente Nozionale Idrocarburi, Rome, Italy

[21] Appl. No.: 188,074

[22] Filed: Sep. 17, 1980

[30] Foreign Application Priority Data

Oct. 17, 1979 [IT] Italy .................................. 26547 A/79

[51] Int. Cl.$^3$ ............................................. C07B 19/02
[52] U.S. Cl. ................................................... 435/280
[58] Field of Search ......................................... 435/280

[56] References Cited

U.S. PATENT DOCUMENTS 4,065,353 12/1977 Cecere et al. ................... 435/280 X
4,237,227 12/1980 Yamada et al. ................. 435/280 X
4,242,452 12/1980 Yamada et al. ................. 435/280 X

OTHER PUBLICATIONS

Jesse P. Greenstein and Milton Winitz, Chemistry of the Amino Acids, John Wiley & Sons, Inc., vol. 2, pp. 860–863, 1961.

Chemical Abstracts, vol. 91, 170502m, 1979.

*Primary Examiner*—Robert J. Warden
*Attorney, Agent, or Firm*—Morgan, Finnegan, Pine, Foley & Lee

[57] ABSTRACT

This invention relates to a process for preparing carbamyl derivatives of α-hydroxy acids by the hydrolysis of 5-substituted 2,4-oxazolidinediones.

The carbamyl derivatives can be further hydrolyzed to α-hydroxy acids.

The invention also relates to a process for the enzymatic hydrolysis of racemic 5-substituted 2,4-oxazolidinediones to give only one of the two possible optical isomers, i.e. the D-carbamyl-α-hydroxy acid. The free D-α-hydroxy acid can be obtained from the optically active carbamyl derivative by simple hydrolysis. Of particular interest is the case in which the D-α-hydroxy acid is D(−)mandelic acid. The enzymatic activity required for preparing the carbamyl derivative of D(−)mandelic acid has been found both in homogenized veal liver and in a series of microorganisms, including *Agrobacterium radiobacter, Bacillus brevis, Bacillus stearothermophilus*, Pseudomonas sp., *Pseudomonas desmolytica, Pseudomonas fluorescens, Pseudomonas putida*.

6 Claims, No Drawings

PROCESS FOR PREPARING CARBAMYL DERIVATIVES OF α-HYDROXY ACIDS AND THE CORRESPONDING α-HYDROXY ACIDS

This invention relates to a process for preparing α-hydroxy acids by the hydrolysis of compounds of general formula (I):

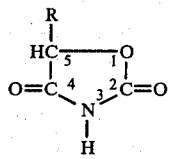

where R can be a substituted or unsubstituted aromatic or aliphatic residue.

According to the present invention, the compounds of general formula (I), i.e. 5-substituted 2,4-oxazolidinediones, can undergo a hydrolysis reaction which opens the ring in accordance with the following scheme:

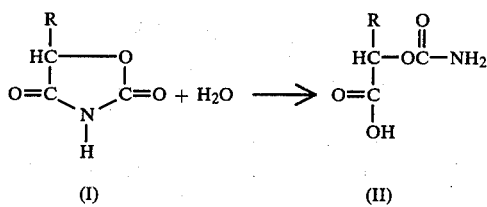

The compound of general formula (II) obtained by hydrolysis is the carbamyl derivative of a α-hydroxy acid, from which the α-hydroxy acid can be obtained by subjecting compound (II) to further hydrolysis in accordance with the scheme:

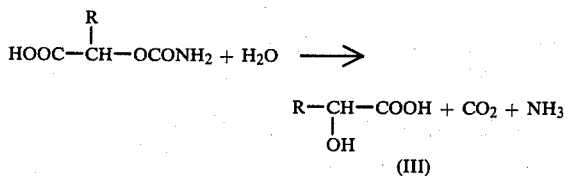

The final product (III) is the α-hydroxy acid. A further important subject matter of the present invention is a process for the direct production of D-carbamyl-α-hydroxy acids by the steroselective enzymatic hydrolysis of racemic mixtures of compounds of general formula (I). In this respect, it has been surprisingly found possible to enzymatically hydrolyse 5-substituted DL-2,4-oxazolidinediones in such a manner as to give only the D-carbamyl-α-hydroxy acid, i.e. only one of the two possible optical isomers. The free α-hydroxy acid of D configuration can be obtained from the optically active carbamyl derivative by simple hydrolysis. Compounds such as those described in formula (I) can be easily prepared from the corresponding α-hydroxy acids by reacting them with urea as described by Helge Aspelund in Acta Acad. Aboensins Math. and Phys. 22 (7) 12 (1961). Resolution of the racemic mixture is effected by stereoselective hydrolysis of the oxazolidine ring carried out by enzymes easily obtainable from cultures of various microorganisms or from extracts of animal organs such as veal liver. One particular case, which is extremely interesting but does not limit the general validity of the aforesaid process, is the preparation of D (−) mandelic acid

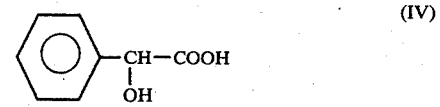

which is an important intermediate in the preparation of semisynthetic antibiotics.

This intermediate is generally prepared by resolution of the racemic mixture by means of the formation of diastereo-isomer salts with optically active natural bases such as brucine. These processes in any case give a maximum theoretical yield of 50% in that the L enantiomer must be racemised before being recycled.

According to the present invention, the carbamyl derivative of D(−) mandelic acid can be advantageously prepared by the stereoselective enzymatic hydrolysis of the corresponding 5-phenyl-2,4-oxazolidinedione. A further considerable advantage of the process according to the present invention is that the enzymatic reaction substrate racemises spontaneously under the hydrolysis conditions, so that at the end of the reaction the carbamate of the D-mandelic acid is obtained in a stoichiometric quantity with respect to the starting substrate.

The reaction scheme is as follows:

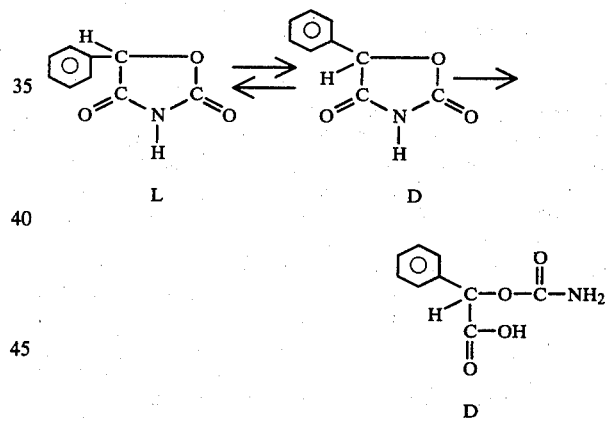

D(−) mandelic acid is then obtained from the D-mandelic acid carbamate by hydrolysis in an acid environment.

The enzymatic activity required for preparing the D(−) mandelic acid carbamate has been found both in homogenised veal liver and in the following microorganisms: Pseudomonas, Archromobacter, Corynebacterium, Brevibacterium, Microbacterium, Arthrobacter, Agrobacterium, Aerobacter, Klebsiella, Serratia, Proteus, Bacillus, Micrococcus, Sarcina, Protaminobacter, Streptomyces, Actinomyces, Candida, Rhodotorula, Pichia and Paecilomyces.

Microorganisms of the following kinds have proved particularly suitable:
*Agrobacterium radiobacter* NRRL B 11291
*Bacillus Brevis* NRRL B 11080
*Bacillus stearothermophilus* NRRL B 11079
Pseudomonas sp CBS 145.75
Pseudomonas sp CBS 146.75

Pseudomonas sp ATCC 11299
*Pseudomonas desmolytica* NCIB8859
*Pseudomonas fluorescens* ATCC 11250
*Pseudomonas putida* ATCC 12633

In carrying out the process according to the present invention, the microorganisms of the aforesaid types are cultivated under aerobic conditions in culture media containing sources of nitrogen, carbon, phosphorus and mineral salts at a temperature of between 20° C. and 80° C. for a time of between 10 and 72 hours and at a pH of between 6.0 and 8.0.

Glucose, lactate, acetate, corn steep liquor and lactose can be used as sources of carbon.

Hydrolysed meat, casein or soya, ammonium salts, urea, hydrantoin etc. can be used as sources of nitrogen.

A suitable culture medium has, for example, the following composition:

| | |
|---|---|
| Meat peptone | 5 g |
| Meat extract | 5 g |
| Glucose | 5 g |
| Distilled water | 1000 cc |
| pH | 7.0 ÷ 7.2 |

The D(−) carbamate of mandelic acid can be produced directly in the fermentation media containing the corresponding DL-2,4-oxazolidinedione, or can be produced by directly using the microbic paste as resting cells or by using extracts thereof. The enzymatic complexes of the present invention are extracted from the bacterial paste by the normal methods used in enzymology.

For this purpose the cells are disintegrated using suitable apparatus such as the French Pressure-Cell Press, Manton Gaulin Homogenizer, rotatory disintegrators etc., or using ultrasonics.

Hydrolysis of the 5-substituted D,L-2,4-oxazolidinedione can be carried out by adding the enzyme in the following forms to the reaction mixture: fresh cells, lyophilised cells, toluenised cells, acetonic powder or crude or purified extracts. A further technical and economical improvement can be made by immobilising the enzymes by way of combination with macromolecular compounds by forming chemical bonds with the matrix or ionic bonds, or by physical immobilisation.

The examples given hereinafter describe other methods of effecting the present invention, but are not limitative thereof.

EXAMPLE 1

A culture broth was prepared having the following combination:

| | |
|---|---|
| Meat peptone | 5 g |
| Meat extract | 3 g |
| Glucose | 5 g |
| Distilled water | 1000 cc |

The pH was adjusted to 7.2 with soda, and the medium was distributed into 500 ml flasks in portions of 100 ml. After sterilising for 30 minutes at 110° C., the flasks were innoculated with a culture of the Pseudomonas CBS 145.75 slant strain containing the same medium with 2% of agar (DIFCO) and incubated for 24 hours at 30° C. under orbital stirring (220 r.p.m.).

1 ml of this preculture (D.O. at 550 nm=0.250 dil×1:10) was placed in five 500 ml flasks containing 100 ml of the same medium, and the culture was incubated at 30° C. under orbital stirring (220 r.p.m.) for 24 hours (D.O. at 550 nm=0.450 dil 1:10).

The cells were then collected, washed in physiological solution and finally suspended in 100 ml of 0.1 M pyrophosphate buffer of pH 8.7 containing 2 g of DL 5-phenyl-2,4-oxazolidinedione at a temperature of 50° C.

After 70 hours of incubation under these conditions, hydrolysis to the D-mandelic acid carbamate was completed, as proved by polarimetric analysis of the reaction mixture.

The carbamate was isolated from the reaction mixture after removing the cellular paste by centrifuging, then cooled and the pH adjusted to 2.5 with concentrated HCl. The precipitate so obtained was filtered, washed with cold $H_2O$ and dried under vacuum. 1.8 g of carbamate were obtained, its identity being proved by I.R. and NMR spectra and by elementary analysis.

The specific optical rotatory power, $[\alpha]_D^{25}$, of the alcoholic solution of the carbamate obtained as heretofore described was −141.

Its melting point (with decomposition) was 169° C.

1.4 grams of carbamate were suspended in 100 ml of $H_2O$, then heated under reflux for 4 hours. The aqueous solution thus obtained was acidified and then extracted with ethyl ether, and the organic phase was concentrated under vacuum to dryness. 1.10 grams of crude mandelic acid were obtained having a $[\alpha]_D^{25}$ of −120 (optical yield 76%).

When crystallised from water, the crude product had a M.P. of 130° C. and a $[\alpha]_D^{25}$ of −154.5 in water, against a M.P. of 133° C. and a $[\alpha]_D^{25}$ of −158 as described in the literature for D(−) mandelic acid.

EXAMPLE 2

1 g of acetonic powder of homogenised veal liver was added to a solution containing 500 mg of DL-5-phenyl-2,4-oxazolidinedione in 50 ml of 0.1 M pyrophosphate buffer having a pH of 8.5.

The reaction mixture so obtained was incubated at 30° C. for 40 hours.

The D mandelic acid carbamate was then recovered as described in example 1.

380 mg of crude carbamate were obtained having a specific optical rotatory power, $[\alpha]_D^{25}$, of −136 is ethanol. Acid hydrolysis of the crude carbamate was then carried out, and the mandelic acid was extracted as described in example 1, to give 300 mg of crude D mandelic acid having a $[\alpha]_D^{25}$ of −116 (optical yield 73.5%).

We claim:

1. A process for preparing D-carbamyl-α-hydroxy acids of the formula

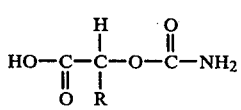

consisting of subjecting 5-substituted DL-2,4-oxazolidinediones of the general formula:

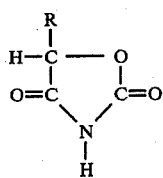

where R is a substituted or unsubstituted aromatic or aliphatic residue, to stereoselective enzymatic hydrolysis in the presence of an agent produced from microorganisms of the following types:
(a) *Agrobacterium radiobacter* NRRL B 11291,
(b) *Bacillus brevis* NRRL B 11080,
(c) *Bacillus stearothermophilus* NRRL B 11079,
(d) Pseudomonas sp CBS 145.75,
(e) Pseudomonas sp CBS 146.75,
(f) Pseudomonas sp ATCC 11299,
(g) *Pseudomonas desmolytica* NC1B8859,
(h) *Pseudomonas fluorescens* ATCC 11250, and
(i) *Pseudomonas putida* ATCC 12633.

2. A process for preparing D-carbamyl-α-hydroxy acids as claimed in claim 1, wherein the agents having enzymatic activity in the stereoselective hydrolysis of 5-substituted 2,4-oxazolidinediones are obtained from homogenised veal liver.

3. A process for preparing D-carbamyl-α-hydroxy acids as claimed in claim 1, wherein the microorganisms are cultivated under aerobic conditions at a temperature of 20° C. and 80° C.

4. A process for preparing D-carbamyl-α-hydroxy acids as claimed in claim 1, wherein the microorganism cultivation time is between 10 and 72 hours.

5. A process for preparing D-carbamyl-α-hydroxy acids as claimed in claim 1, wherein the pH of the microorganism culture medium lies within the range 6–8.

6. A process for preparing D-carbamyl-α-hydroxy acids as claimed in claim 1, wherein the D-α-hydroxy acid is D(−) mandelic acid, and the substrate of general formula (I) is DL-5-phenyl-2,4-oxazolidinedione.

* * * * *